(12) United States Patent
Fuchs et al.

(10) Patent No.: US 8,031,931 B2
(45) Date of Patent: Oct. 4, 2011

(54) PRINTED FOURIER FILTERING IN OPTICAL INSPECTION TOOLS

(75) Inventors: Dan T. Fuchs, Tel Aviv (IL); Shai Silberstein, Risbon Le-Zion (IL)

(73) Assignee: Applied Materials South East Asia Pte. Ltd., Singapore (SG)

( * ) Notice: Subject to any disclaimer, the term of this patent is extended or adjusted under 35 U.S.C. 154(b) by 1080 days.

(21) Appl. No.: 11/410,276

(22) Filed: Apr. 24, 2006

(65) Prior Publication Data

US 2007/0247668 A1    Oct. 25, 2007

(51) Int. Cl.
*G06K 9/00* (2006.01)

(52) U.S. Cl. ........ 382/145; 382/141; 382/144; 382/149; 382/152; 356/237.1; 356/237.2; 356/237.3; 356/237.4; 356/237.5; 356/237.6; 356/239.1; 356/239.3; 356/239.7; 356/239.8

(58) Field of Classification Search .................. 382/141, 382/144, 145, 149, 152; 356/237.1, 237.2, 356/237.3, 237.4, 237.5, 237.6, 239.1, 239.3, 356/239.7, 239.8

See application file for complete search history.

(56) References Cited

U.S. PATENT DOCUMENTS

| | | | |
|---|---|---|---|
| 3,220,331 A * | 11/1965 | Evans et al. .................. 355/78 |
| 3,598,467 A | 8/1971 | Pearson |
| 3,790,280 A | 2/1974 | Heinz et al. |
| 4,011,403 A | 3/1977 | Epstein et al. |
| 4,247,203 A | 1/1981 | Levy et al. |
| 4,323,925 A | 4/1982 | Abell et al. |
| 4,347,001 A | 8/1982 | Levy et al. |
| 4,360,372 A | 11/1982 | Maciejko |
| 4,378,159 A | 3/1983 | Galbraith |
| 4,415,240 A | 11/1983 | Nishioka et al. |
| 4,462,662 A | 7/1984 | Lama |
| 4,486,776 A | 12/1984 | Yoshida |
| 4,532,650 A | 7/1985 | Wihl et al. |
| 4,556,317 A | 12/1985 | Sandland et al. |
| 4,579,455 A | 4/1986 | Levy et al. |

(Continued)

FOREIGN PATENT DOCUMENTS

EP    0 557 558    9/1993

(Continued)

OTHER PUBLICATIONS

Article—*Inspection of Integrated Circuit Photomasks with Intensity Special Filters*, L. S. Watkins, Proceedings of the IEEE, vol. 37, No. 9, Sep. 1969, pp. 1634-1639.

(Continued)

*Primary Examiner* — Bhavesh Mehta
*Assistant Examiner* — Daniel Zeilberger
(74) *Attorney, Agent, or Firm* — SNR Denton US LLP

(57) ABSTRACT

A spatial mask printer may be used in conjunction with an optical inspection tool. The tool can be used to obtain a Fourier image of an inspected object, and a filter mask image can be designed to block certain aspects of the object's image in the Fourier plane corresponding to repetitive aspects of the imaged object. The filter mask image can then be printed and used in the tool during the inspection process. The mask image may be designed by hand or by computer and may be stored for later use. Filters may be automatically placed into the optical path of the inspection tool by a filter wheel, or may be housed in other filter banks. The printer may be configured to operate in a clean room environment, and may be integrated into the optical inspection tool.

21 Claims, 9 Drawing Sheets

U.S. PATENT DOCUMENTS

| | | |
|---|---|---|
| 4,588,293 A | 5/1986 | Axelrod |
| 4,589,736 A | 5/1986 | Harrigan et al. |
| 4,597,665 A | 7/1986 | Galbraith et al. |
| 4,601,576 A | 7/1986 | Galbraith |
| 4,610,513 A | 9/1986 | Nishioka et al. |
| 4,618,938 A | 10/1986 | Sandland |
| 4,619,508 A | 10/1986 | Shibuya et al. |
| 4,639,587 A | 1/1987 | Chadwick et al. |
| 4,644,172 A | 2/1987 | Sandland et al. |
| 4,725,722 A | 2/1988 | Maeda et al. |
| 4,734,923 A | 3/1988 | Frankel et al. |
| 4,760,265 A | 7/1988 | Yoshida et al. |
| 4,763,975 A | 8/1988 | Scifres et al. |
| 4,766,324 A | 8/1988 | Saadat et al. |
| 4,805,123 A | 2/1989 | Specht et al. |
| 4,806,774 A | 2/1989 | Lin et al. |
| 4,845,558 A | 7/1989 | Tsai et al. |
| 4,877,326 A | 10/1989 | Chadwick et al. |
| 4,898,471 A | 2/1990 | Vaught et al. |
| 4,929,081 A | 5/1990 | Yamamoto et al. |
| 4,964,692 A | 10/1990 | Prescott |
| 4,967,095 A | 10/1990 | Berger et al. |
| 4,969,198 A | 11/1990 | Batchelder et al. |
| 5,008,743 A | 4/1991 | Katzir et al. |
| 5,012,081 A | 4/1991 | Jungwirth et al. |
| 5,029,975 A | 7/1991 | Pease |
| 5,038,048 A | 8/1991 | Maeda et al. |
| 5,046,847 A | 9/1991 | Nakata et al. |
| 5,056,765 A | 10/1991 | Branstater |
| 5,058,982 A | 10/1991 | Katzir |
| 5,076,692 A | 12/1991 | Neukermans et al. |
| 5,112,129 A | 5/1992 | Davidson et al. |
| 5,153,668 A | 10/1992 | Katzir et al. |
| 5,172,000 A | 12/1992 | Scheff et al. |
| 5,177,559 A | 1/1993 | Batchelder et al. |
| 5,185,812 A | 2/1993 | Yamashita et al. |
| 5,194,959 A | 3/1993 | Kaneko et al. |
| 5,233,460 A | 8/1993 | Partlo et al. |
| 5,264,912 A | 11/1993 | Vaught et al. |
| 5,267,017 A | 11/1993 | Uritsky et al. |
| 5,276,498 A | 1/1994 | Galbraith et al. |
| 5,302,999 A | 4/1994 | Oshida et al. |
| 5,381,004 A | 1/1995 | Uritsky et al. |
| 5,386,228 A | 1/1995 | Okino |
| 5,422,724 A | 6/1995 | Kinney et al. |
| 5,432,331 A | 7/1995 | Wertheimer |
| 5,461,237 A | 10/1995 | Wakamoto et al. |
| 5,469,274 A | 11/1995 | Iwasaki et al. |
| 5,471,066 A | 11/1995 | Hagiwara |
| 5,471,341 A | 11/1995 | Warde et al. |
| 5,506,676 A | 4/1996 | Hendler et al. |
| 5,537,669 A | 7/1996 | Evans et al. |
| 5,583,632 A | 12/1996 | Haga |
| 5,586,058 A | 12/1996 | Aloni et al. |
| 5,589,862 A * | 12/1996 | Ujita et al. .................... 347/87 |
| 5,604,585 A | 2/1997 | Johnson et al. |
| 5,608,155 A | 3/1997 | Ye et al. |
| 5,617,203 A | 4/1997 | Kobayashi et al. |
| 5,619,429 A | 4/1997 | Aloni et al. |
| 5,619,588 A | 4/1997 | Yolles et al. |
| 5,629,768 A | 5/1997 | Hagiwara |
| 5,659,172 A | 8/1997 | Wagner et al. |
| 5,659,390 A | 8/1997 | Danko |
| 5,661,575 A | 8/1997 | Yamashita et al. |
| 5,689,592 A | 11/1997 | Ericsson et al. |
| 5,694,481 A | 12/1997 | Lam et al. |
| 5,699,447 A | 12/1997 | Alumot et al. |
| 5,784,189 A | 7/1998 | Bozler et al. |
| 5,797,317 A | 8/1998 | Lahat et al. |
| 5,798,829 A | 8/1998 | Vaez-Iravani |
| 5,822,055 A | 10/1998 | Tsai et al. |
| 5,825,482 A | 10/1998 | Nikoonahad et al. |
| 5,835,225 A | 11/1998 | Thakur et al. |
| 5,835,278 A | 11/1998 | Rubin et al. |
| 5,859,698 A | 1/1999 | Chau |
| 5,864,394 A | 1/1999 | Jordan, III et al. |
| 5,872,862 A | 2/1999 | Okubo et al. |
| 5,883,710 A | 3/1999 | Nikoonahad et al. |
| 5,892,579 A | 4/1999 | Elyasaf et al. |
| 5,907,628 A | 5/1999 | Yolles et al. |
| 5,909,276 A | 6/1999 | Kinney et al. |
| 5,912,735 A | 6/1999 | Xu |
| 5,917,588 A | 6/1999 | Addiego |
| 5,939,647 A | 8/1999 | Chinn et al. |
| 5,970,168 A | 10/1999 | Montesanto et al. |
| 5,982,921 A | 11/1999 | Alumot et al. |
| 5,991,699 A | 11/1999 | Kulkarni et al. |
| 5,995,665 A | 11/1999 | Maeda et al. |
| 6,008,786 A | 12/1999 | Kimura et al. |
| 6,020,957 A * | 2/2000 | Rosengaus et al. ........ 356/237.4 |
| 6,021,214 A | 2/2000 | Evans et al. |
| 6,023,056 A | 2/2000 | Fiete et al. |
| 6,064,517 A | 5/2000 | Chuang et al. |
| 6,075,375 A | 6/2000 | Burkhart et al. |
| 6,078,386 A | 6/2000 | Tsai et al. |
| 6,081,325 A | 6/2000 | Leslie et al. |
| 6,081,381 A | 6/2000 | Shalapenok et al. |
| 6,099,596 A | 8/2000 | Li et al. |
| 6,101,271 A | 8/2000 | Yamashita et al. |
| 6,122,046 A | 9/2000 | Almogy |
| 6,124,924 A | 9/2000 | Feldman et al. |
| 6,133,981 A * | 10/2000 | Semba ............................ 355/27 |
| 6,134,365 A | 10/2000 | Colvin |
| 6,147,664 A | 11/2000 | Hansen |
| 6,169,282 B1 | 1/2001 | Maeda et al. |
| 6,170,973 B1 | 1/2001 | Benedict |
| 6,172,349 B1 | 1/2001 | Katz et al. |
| 6,175,645 B1 | 1/2001 | Elyasaf et al. |
| 6,175,646 B1 | 1/2001 | Schemmel et al. |
| 6,178,257 B1 | 1/2001 | Alumot et al. |
| 6,201,601 B1 | 3/2001 | Vaez-Irvani et al. |
| 6,208,411 B1 | 3/2001 | Vaez-Iravani |
| 6,208,750 B1 | 3/2001 | Tsadka |
| 6,215,551 B1 | 4/2001 | Nikoonahad et al. |
| 6,226,116 B1 | 5/2001 | Dowe et al. |
| 6,236,454 B1 | 5/2001 | Almogy |
| 6,246,822 B1 | 6/2001 | Kim et al. |
| 6,249,630 B1 | 6/2001 | Stock et al. |
| 6,250,778 B1 | 6/2001 | Doumuki |
| 6,256,093 B1 | 7/2001 | Ravid et al. |
| 6,267,005 B1 | 7/2001 | Samsavar et al. |
| 6,268,093 B1 | 7/2001 | Kenan et al. |
| 6,268,916 B1 | 7/2001 | Lee et al. |
| 6,271,916 B1 | 8/2001 | Marxer et al. |
| 6,274,878 B1 | 8/2001 | Li et al. |
| 6,282,309 B1 | 8/2001 | Emercy |
| 6,285,400 B1 | 9/2001 | Hokari |
| 6,288,780 B1 | 9/2001 | Fairley et al. |
| 6,292,228 B1 | 9/2001 | Cho |
| 6,317,514 B1 | 11/2001 | Reinhorn et al. |
| 6,324,298 B1 | 11/2001 | O'Dell et al. |
| 6,347,173 B1 | 2/2002 | Suganuma et al. |
| 6,360,005 B1 | 3/2002 | Aloni et al. |
| 6,361,910 B1 | 3/2002 | Sarig et al. |
| 6,366,315 B1 | 4/2002 | Drescher |
| 6,369,888 B1 | 4/2002 | Karpol et al. |
| 6,392,747 B1 | 5/2002 | Allen et al. |
| 6,456,420 B1 | 9/2002 | Goodwin-Johansson |
| 6,456,769 B1 | 9/2002 | Furusawa et al. |
| 6,504,948 B1 | 1/2003 | Schemmel et al. |
| 6,536,882 B1 * | 3/2003 | Hawkins et al. ................ 347/77 |
| 6,563,653 B2 | 5/2003 | Ramm et al. |
| 6,618,093 B1 | 9/2003 | Levy |
| 6,627,865 B1 | 9/2003 | Hamilton |
| 6,628,681 B2 | 9/2003 | Kubota et al. |
| 6,630,996 B2 | 10/2003 | Rao et al. |
| 6,633,375 B1 | 10/2003 | Veith et al. |
| 6,657,157 B1 * | 12/2003 | Altman et al. ........... 219/121.68 |
| 6,657,714 B2 | 12/2003 | Almogy et al. |
| 6,686,602 B2 | 2/2004 | Some |
| 6,686,994 B2 | 2/2004 | Wilk et al. |
| 6,686,995 B2 | 2/2004 | Wilk et al. |
| 6,693,664 B2 | 2/2004 | Neumann |
| 6,707,544 B1 | 3/2004 | Hunter et al. |
| 6,710,868 B2 | 3/2004 | Guetta |
| 6,724,473 B2 | 4/2004 | Leong et al. |
| 6,774,991 B1 | 8/2004 | Danko |

| | | | |
|---|---|---|---|
| 6,781,688 B2 | 8/2004 | Kren et al. | |
| 6,791,072 B1 | 9/2004 | Prabhu | |
| 6,796,699 B2 | 9/2004 | Birk et al. | |
| 6,798,505 B2 | 9/2004 | Karpol et al. | |
| 6,816,249 B2 | 11/2004 | Fairley et al. | |
| 6,818,459 B2 | 11/2004 | Wack et al. | |
| 6,892,013 B2 | 5/2005 | Furman et al. | |
| 6,895,149 B1 | 5/2005 | Jacob et al. | |
| 6,906,794 B2 | 6/2005 | Tsuji | |
| 6,919,958 B2 | 7/2005 | Stanke et al. | |
| 6,924,891 B2 | 8/2005 | Karpol et al. | |
| 6,941,007 B1 | 9/2005 | Do | |
| 6,947,587 B1 | 9/2005 | Maeda et al. | |
| 6,985,184 B2 | 1/2006 | Sato | |
| 7,102,743 B2 | 9/2006 | Tsuji et al. | |
| 7,265,900 B2 | 9/2007 | Korngut et al. | |
| 7,630,069 B2 | 12/2009 | Naftali et al. | |
| 2001/0033386 A1 | 10/2001 | Kranz et al. | |
| 2002/0037099 A1 | 3/2002 | Ogawa et al. | |
| 2002/0054291 A1 | 5/2002 | Tsai et al. | |
| 2002/0067478 A1 | 6/2002 | Karpol et al. | |
| 2002/0171028 A1 | 11/2002 | Feldman | |
| 2002/0191066 A1* | 12/2002 | Bouchard et al. | 347/172 |
| 2003/0048957 A1 | 3/2003 | Dai et al. | |
| 2003/0184739 A1 | 10/2003 | Wilk et al. | |
| 2003/0202178 A1 | 10/2003 | Tsuji et al. | |
| 2003/0210391 A1 | 11/2003 | Uto et al. | |
| 2003/0227617 A1 | 12/2003 | Yoshida et al. | |
| 2003/0227618 A1 | 12/2003 | Some | |
| 2004/0032581 A1 | 2/2004 | Nikoonahad et al. | |
| 2004/0057611 A1 | 3/2004 | Lee | |
| 2004/0066507 A1 | 4/2004 | Kren et al. | |
| 2004/0105093 A1* | 6/2004 | Hamamatsu et al. | 356/237.4 |
| 2004/0136665 A1 | 7/2004 | Furman et al. | |
| 2004/0146295 A1 | 7/2004 | Furman et al. | |
| 2004/0252297 A1 | 12/2004 | Fairley et al. | |
| 2005/0062960 A1 | 3/2005 | Tsuji et al. | |
| 2005/0084766 A1 | 4/2005 | Sandstrom | |
| 2005/0110987 A1 | 5/2005 | Furman et al. | |
| 2005/0114823 A1* | 5/2005 | Kuchler et al. | 716/21 |
| 2005/0180707 A1 | 8/2005 | Furman et al. | |
| 2005/0195389 A1 | 9/2005 | Noy et al. | |
| 2006/0007434 A1 | 1/2006 | Furman et al. | |
| 2006/0012781 A1 | 1/2006 | Fradkin et al. | |
| 2006/0193506 A1 | 8/2006 | Dorphan et al. | |
| 2006/0193507 A1 | 8/2006 | Sali | |

FOREIGN PATENT DOCUMENTS

| | | |
|---|---|---|
| EP | 0 959 378 | 11/1999 |
| JP | 61262607 | 11/1986 |
| WO | WO 00/70332 | 11/2000 |
| WO | WO 2004/031753 | 4/2004 |
| WO | WO 2005022969 A2 * | 3/2005 |

OTHER PUBLICATIONS

Article—*Intensity Spatial Filtering Applied to Defect Detection in Integrated Photomasks*, N. N. Axelrod et al., Proceeding of the IEEE, Apr. 1972, pp. 447-448.
Article—*Real-Time Defect Inspection of Periodic Patterns Using Self-Pumped Barium Titanate Crystal*, Ghosh et al., Optics Communications, vol. 77, No. 2,3, Jun. 15, 1990, pp. 135-138.
Office Action dated Aug. 12, 2005, from U.S. Appl. No. 10/345,097, filed Jan. 15, 2003, 21 pages.
Response to Office Action filed Jan. 13, 2006, from U.S. Appl. No. 10/345,097, filed Jan. 15, 2003, 6 pages.
Final Office Action dated Apr. 6, 2006, from U.S. Appl. No. 10/345,097, filed Jan. 15, 2003, 8 pages.
Response to Final Office Action filed Jul. 6, 2006, from U.S. Appl. No. 10/345,097, filed Jan. 15, 2003, 8 pages.
Office Action dated Sep. 7, 2006, from U.S. Appl. No. 10/345,097, filed Jan. 15, 2003, 9 pages.
Response to Office Action filed Mar. 9, 2007, from U.S. Appl. No. 10/345,097, filed Jan. 15, 2003, 14 pages.
Final Office Action dated May 29, 2007, from U.S. Appl. No. 10/345,097, filed Jan. 15, 2003, 9 pages.
Response to Final Office Action filed Oct. 1, 2007, from U.S. Appl. No. 10/345,097, filed Jan. 15, 2003, 10 pages.
Response to Final Office Action filed Nov. 29, 2007, from U.S. Appl. No. 10/345,097, filed Jan. 15, 2003, 6 pages.
Office Action dated Mar. 4, 2008, from U.S. Appl. No. 10/345,097, filed Jan. 15, 2003, 10 pages.
Response to Office Action filed Aug. 25, 2008, from U.S. Appl. No. 10/345,097, filed Jan. 15, 2003, 9 pages.
Office Action dated Oct. 20, 2005, from U.S. Appl. No. 11/021,393, filed Dec. 23, 2004, 18 pages.
Response to Office Action filed Jan. 24, 2006, from U.S. Appl. No. 11/021,393, filed Dec. 23, 2004, 12 pages.
Office Action dated Feb. 8, 2007, from U.S. Appl. No. 11/476,356, filed Jun. 28, 2006 ,16 pages.
Response to Office Action filed May 7, 2007, from U.S. Appl. No. 11/476,356, filed Jun. 28, 2006, 10 pages.
Final Office Action dated Jul. 7, 2007, from U.S. Appl. No. 11/476,356, filed Jun. 28, 2006, 5 pages.
Office Action dated Aug. 6, 2008, from U.S. Appl. No. 11/476,358, filed Jun. 28, 2006, 16 pages.
Response to Office Action filed Sep. 24, 2008, from U.S. Appl. No. 11/476,358, filed Jun. 28, 2006, 7 pages.
Office Action dated Apr. 2, 2009, from U.S. Appl. No. 11/476,358, filed Jun. 28, 2006), 9 pages.
Office Action dated Jan. 28, 2008, from U.S. Appl. No. 11/476,322, filed Jun. 28, 2006, 18 pages.
Response to Office Action filed Apr. 23, 2008, from U.S. Appl. No. 11/476,322, filed Jun. 28, 2006, 11 pages.
Office Action dated May 29, 2008, from U.S. Appl. No. 11/524,684, filed Sep. 21, 2006, 26 pages.
Response to Office Action filed Aug. 25, 2008, from U.S. Appl. No. 11/524,684, filed Sep. 21, 2006, 16 pages.
Final Office Action dated Dec. 22, 2008, from U.S. Appl. No. 11/524,684, filed Sep. 21, 2006, 15 pages.
Response to Final Office Action filed Jun. 10, 2009, from U.S. Appl. No. 11/524,684, filed Sep. 21, 2006, 6 pages.
European Search Report and Opinion Dated Dec. 1, 2009, from EP Patent Application No. 06251044.1, 4pp.
Negevtech, Ltd.; PCT/IL04/00022 filed Jan. 11, 2004, International Search Report and Written Opinion dated Nov. 8, 2004, ISA/US, 6pp.
Negevtech, Ltd.; PCT/IL04/00022 filed Jan. 11, 2004, International Preliminary Report on Patentability dated Jul. 15, 2005,. WIPO, 5pp.
U.S. Appl. No. 60/415,082, filed Sep. 30, 2002, 19pp.
Office Action dated Apr. 27, 2009, from U.S. Appl. No. 11/764,296, filed Jun. 18, 2007, 14 pages.
Response to Office Action filed Jul. 24, 2009, from U.S. Appl. No. 11/764,296, filed Jun. 18, 2007, 12 pages.
Final Office Action dated Oct. 28, 2009, from U.S. Appl. No. 11/764,296, filed Jun. 18, 2007, 15 pages.
Response to Final Office Action filed Jan. 21, 2010, from U.S. Appl. No. 11/764,296, filed Jun. 18, 2007, 12 pages.
Office Action dated Mar. 17, 2010, from U.S. Appl. No. 11/764,296, filed Jun. 18, 2007, 11 pages.
Response to Office Action filed Jun. 15, 2010, from U.S. Appl. No. 11/764,296, filed Jun. 18, 2007, 10 pages.
Office Action dated Nov. 5, 2009, from U.S. Appl. No. 12/471,752, filed May 26, 2009, 18 pages.
Response to Office Action filed Feb. 5, 2010, from U.S. Appl. No. 12/471,752, filed May 26, 2009, 17 pages.
Final Office Action dated May 5, 2010, from U.S. Appl. No. 12/471,752, filed May 26, 2009, 20 pages.
Office Action dated Feb. 21, 2008, from U.S. Appl. No. 11/684,191, filed Mar. 9, 2007, 26 pages.
Response to Office Action filed May 9, 2008, from U.S. Appl. No. 11/684,191, filed Mar. 9, 2007, 14 pages.
Office Action dated Aug. 15, 2008, from U.S. Appl. No. 11/684,191, filed Mar. 9, 2007, 19 pages.
Response to Office Action filed Oct. 29, 2008, from U.S. Appl. No. 11/684,191, filed Mar. 9, 2007, 31 pages.
Final Office Action dated Jan. 26, 2009, from U.S. Appl. No. 11/684,191, filed Mar. 9, 2007, 23 pages.
Response to Final Office Action filed Jul. 24, 2009, from U.S. Appl. No. 11/684,191, filed Mar. 9, 2007, 7 pages.
Office Action dated Jul. 23, 2004, from U.S. Appl. No. 10/345,096, filed Apr. 2, 2003, 15 pages.

Response to Office Action filed Nov. 24, 2004, from U.S. Appl. No. 10/345,096, filed Apr. 2, 2003, 10 pages.
Office Action dated Dec. 27, 2007, from U.S. Appl. No. 11/068,711, filed Feb. 25, 2005, 19 pages.
Response to Office Action filed Mar. 27, 2008, from U.S. Appl. No. 11/068,711, filed Feb. 25, 2005, 8 pages.
Supplemental Response to Office Action filed May 27, 2008, from U.S. Appl. No. 11/068,711, filed Feb. 25, 2005, 8 pages.
Final Office Action dated Sep. 30, 2008, from U.S. Appl. No. 11/068,711, filed Feb. 25, 2005, 11 pages.
Response to Final Office Action filed Mar. 25, 2009, from U.S. Appl. No. 11/068,711, filed Feb. 25, 2005, 5 pages.
Office Action dated Jun. 8, 2009, from U.S. Appl. No. 11/068,711, filed Feb. 25, 2005, 11 pages.
Response to Office Action filed Sep. 8, 2009, from U.S. Appl. No. 11/068,711, filed Feb. 25, 2005, 5 pages.
Office Action dated Sep. 29, 2009, from U.S. Appl. No. 11/068,711, filed Feb. 25, 2005, 7 pages.
Office Action dated Oct. 11, 2007, from U.S. Appl. No. 11/503,859, filed Aug. 14, 2006, 9 pages.
Response to Office Action filed Jan. 11, 2008, from U.S. Appl. No. 11/503,859, filed Aug. 14, 2006, 15 pages.
Final Office Action dated Feb. 13, 2008, from U.S. Appl. No. 11/503,859, filed Aug. 14, 2006, 8 pages.
Response to Final Office Action filed Apr. 18, 2008, from U.S. Appl. No. 11/503,859, filed Aug. 14, 2006, 12 pages.
Office Action dated May 1, 2008, from U.S. Appl. No. 11/503,859, filed Aug. 14, 2006, 9 pages.
Response to Office Action filed Jul. 15, 2008, from U.S. Appl. No. 11/503,859, filed Aug. 14, 2006, 9 pages.
Final Office Action dated Aug. 19, 2008, from U.S. Appl. No. 11/503,859, filed Aug. 14, 2006, 12 pages.
Office Action dated Sep. 17, 2008, from U.S. Appl. No. 11/069,712, filed Feb. 28, 2005, 53 pages.
Response to Office Action filed Mar. 16, 2009, from U.S. Appl. No. 11/069,712, filed Feb. 28, 2005, 6 pages.
Final Office Action dated Jul. 7, 2009, from U.S. Appl. No. 11/069,712, filed Feb. 28, 2005, 55 pages.
Response to Final Office Action filed Sep. 30, 2009, from U.S. Appl. No. 11/069,712, filed Feb. 28, 2005, 6 pages.
Office Action dated Dec. 11, 2007, from U.S. Appl. No. 11/709,019, filed Feb. 21, 2007, 17 pages.
Response to Office Action filed Feb. 8, 2008, from U.S. Appl. No. 11/709,019, filed Feb. 21, 2007, 18 pages.
Final Office Action dated May 30, 2008, from U.S. Appl. No. 11/709,019, filed Feb. 21, 2007, 8 pages.
Response to Final Office Action filed Aug. 21, 2008, from U.S. Appl. No. 11/709,019, filed Feb. 21, 2007, 13 pages.
Office Action dated Mar. 8, 2006, from U.S. Appl. No. 11/096,873, filed Aug. 21, 2007, 13 pages.
Response to Office Action filed May 30, 2006, from U.S. Appl. No. 11/096,873, filed Aug. 21, 2007, 15 pages.
Supplemental Response to Office Action filed Jul. 11, 2006, from U.S. Appl. No. 11/096,873, filed Aug. 21, 2007, 7 pages.
Final Office Action dated Sep. 27, 2006, from U.S. Appl. No. 11/096,873, filed Aug. 21, 2007, 8 pages.
Response to Final Office Action filed Oct. 20, 2006, from U.S. Appl. No. 11/096,873, filed Aug. 21, 2007, 10 pages.
Response to European Search Report and Opinion filed May 11, 2009, from EP Patent Application No. 07252110.7, 16pp.
European Search Report and Opinion Dated Jul. 11, 2008, from EP Patent Application No. 07252110.7, 15pp.
European Search Report and Opinion Dated Nov. 2, 2007, from EP Patent Application No. 07252110.7, 15pp.
European Partial Search Report and Opinion Dated Sep. 13, 2007, from EP Patent Application No. 07252110.7, 5pp.
European Search Report Apr. 3, 2003, from EP Patent Application No. 03250255, 5pp.
Manassah et al, Spectral Extent and Pulse Shape of the Supercontinuum for Ultrashort Laser Pulse, IEEE Journal of Quantum Electronics, vol. QE-22, No. 1, Jan. 1986, pp. 197-204.
Product Information Sheet, KOHERAS SUPERK™ BLUE, 2pp.
Hansen et al., Supercontinuum Generation in Photonic Crystal Fibers, Crystal Fibre A/S, www.crystal-fibre.com, pp. 1-11.
Photonic Crystal Fibers by Blaze Photonics, 4pp.
Dingel et al., Speckle Reduction With Virtual Incoherent Laser Illumination Using a Modified Fiber Array Optik, Wissenschaftliche Verlag GmbH, Stuttgart, Germany, vol. 94, No. 3, Sep. 1993, pp. 132-136.
Jain, Anil K., Fundamentals of Digital Image Processing, Prentice-Hall, Englewood Cliffs, New Jersey, USA, 1989, pp. 347-350.
Gonzales & Woods, Digital Image Processing, Prentice-Hall, Englewood Cliffs, New Jersey, USA, 2002, pp. 273-275.
S.H. Moseley et al., Programmable 2-Dimensional Microshutter Arrays, published in the ASP Conference Series, vol. XXX, 2000.
T.S. McKecknie, Speckle Reduction, pp. 123-1 70 in Topics in Applied Physics, vol. 9, Laser Speckle and Related Phenomena, edited by J.C. Dainty, Springer Verlag 1984.
D. Kohler et al., Speckle Reduction in Pulsed-Laser Photography, published in Optics Communications, vol. 12, No. 1, pp. 24-28, Sep. 1974.
"Machine Vision and Applications", 1998 1 :205-221, by IBM Scientists Byron E. Dom, et al.
Negevtech, Ltd.; PCT/IL04/00023 filed Jan. 11, 2004, International Search Report and Written Opinion dated Sep. 12, 2007. ISA/US, 8pp.
Patent Abstracts of Japan, vol. 1997, No. 03, Mar. 1997 & JP 08 292361.
Patent Abstracts of Japan, vol. 17, No. 6 13, Nov. 1993 & JP 05 190421.
Patent Abstracts of Japan, vol. 1996, No. 10, Oct. 1996 & JP 08 154210.
Patent Abstracts of Japan, vol. 1999, No. 04, Apr. 1999 & JP 11 014357.

* cited by examiner

PRINTED FOURIER FILTERING IN OPTICAL INSPECTION TOOLS

BACKGROUND OF THE INVENTION

In the semiconductor industry, devices are fabricated by a number of processes to produce precisely-defined structures of an ever-decreasing size. Even the slightest structural defect can ruin a semiconductor device, and so to avoid losses of time and effort, detection of defects is critical before a defective device is mass-produced or further processes are performed on a defective wafer. Fast, on-line detection of wafer defects is possible through the use of optical wafer inspection systems. For example, in one type of system, a two-dimensional image of a selected field of view of a wafer is obtained, and that field of view is compared to another view which, under ideal conditions, should be identical. The comparison of like fields of view can thus reveal irregularities which could indicate a defect.

Generally speaking, a semiconductor wafer may include a number of repetitive patterns, and any defects in the semiconductor wafer will generally produce a variance in those patterns. To streamline the inspection process, a mask or masks may be configured to block portions of the light corresponding to the repetitive aspects of the wafer. In the resulting comparison of fields of view, the signal corresponding to a defect or other non-blocked feature will thus stand out more readily from the background. Such blocking is generally referred to as "Fourier filtering." See, for example, U.S. Pat. No. 5,970,168, issued to Montesanto et al, for a discussion of one type of Fourier filter.

However, prior Fourier filtering methodologies may be less than ideal when utilized in the field. For instance, a high-throughput wafer production facility will have a correspondingly high throughput need for wafer inspections. Fourier filtering in such an environment will require fast, accurate production of appropriate filters for different expected patterns. A reconfigurable filter is one way to meet the high demand for filters in such an environment, but such filters can introduce an additional level of complexity (and thus point of failure) into an already-complex environment. Reconfigurable Fourier filters based on MEMS and LCD technologies have been proposed for use in optical inspection tools, but such filters may not always be practical for certain applications. For instance, both LCD filters and micromirror arrays may have fill factors, extinction ratios, and transmittance characteristics that are less than ideal. Also, light may leak from "closed" micro-elements in a MEMS-based device. Additionally, resolution of reconfigurable filters may be limited by the size of the reconfigurable elements and the size of the filter, such as the number of reconfigurable elements in a row.

Fixed Fourier filters can have higher transmittance, higher resolution, and avoid problems with fill factors. Additionally, fixed filters are generally less physically complex than reconfigurable filters, but require labor and skill to construct. Furthermore, great care must be taken during the construction and use of any filter to avoid the introduction of contaminants to the inspection environment, and to precisely position blocking elements. In the case of a fixed filter, manual construction is not only time-consuming, but generally must be performed outside the inspection cleanroom in order to avoid contaminating the wafer or optical inspection tool.

There remains a need for a Fourier filtering system which can be used for inspecting a variety of wafers with minimal impact on inspection throughput and labor costs.

SUMMARY OF THE INVENTION

A method of producing a spatial filter mask for Fourier filtering is presented, which includes the steps of producing a Fourier image of an object, defining a filter mask image by specifying at least one blocking area corresponding to the Fourier image of a repetitive aspect of the object, and printing a pattern corresponding to the filter mask image on a filter substrate. The Fourier image of the object may be produced by illuminating the object using an optical inspection system and imaging the Fourier plane.

The filter mask image may be defined by drawing, or by using simulations of Fourier images. The filter mask image may be stored as a bitmap or other computer-readable file, and the filter mask image may be printed in UV-curable ink using inkjet, or other printing.

An optical inspection tool including an imager and an object illumination source may be combined with a filter mask printer and positioning apparatus configured to move a filter mask into the Fourier plane of the imager. The positioning apparatus may include conveyors, robotic arms, and other mechanized systems to handle the mask as it is moved into and out of the imager and printer.

The filter masks may be printed using a printer including a loading stage which may hold at least one filter substrate, or a plurality of such substrates. The substrates may be moved using a conveyor to a printing stage including at least one inkjet printing head. The printer components may be housed in a substantially sealed case that includes pressure control and ventilation connections which can be joined with a fab exhaust system so that contaminants and particles within the printer can be evacuated. A curing stage may be included to dry the printed ink. UV-curable ink may be used, and the curing stage may comprise UV lamps.

The system can also include a filter bank which stores a number of filter masks. Such filter banks may comprise, for example, a filter wheel or wheels located in the imager, or a bulk filter storage area outside the imager.

Spatial filter masks disclosed herein may be implemented as filter mask assemblies. The assemblies can include a filter substrate, such as glass, and blocking areas comprising ink, which is printed on the filter substrate in a pattern corresponding to the Fourier image produced by at least one repetitive aspect of a semiconductor device or other object. The substrate may be disposed in a frame, and may be permanently adhered to or removably attached from the frame via spring clips. The filter mask assemblies may also include identification indicia such as barcodes, alphanumeric characters, or radio-frequency identification (RFID) tags.

A method of Fourier filtering is disclosed using a spatial filter mask that is defined based upon the Fourier image of an object and printed on a filter substrate. The mask is then placed in the Fourier plane of the object under inspection, which may be performed by automated machinery such as a filter wheel.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures, in which.

DETAILED DESCRIPTION OF THE INVENTION

Reference will now be made in detail to present embodiments of the present invention, one or more examples of which are illustrated in the accompanying drawings, with like numerals representing substantially identical structural elements. Each example is provided by way of explanation, and not as a limitation. In fact, it will be apparent to those skilled in the art that modifications and variations can be made without departing from the scope or spirit of the disclosure and claims. For instance, features illustrated or described as part of one embodiment may be used on another embodiment to yield a still further embodiment. Thus, it is intended that the invention disclosed herein includes modifications and variations as come within the scope of the appended claims and their equivalents.

Figure 1:
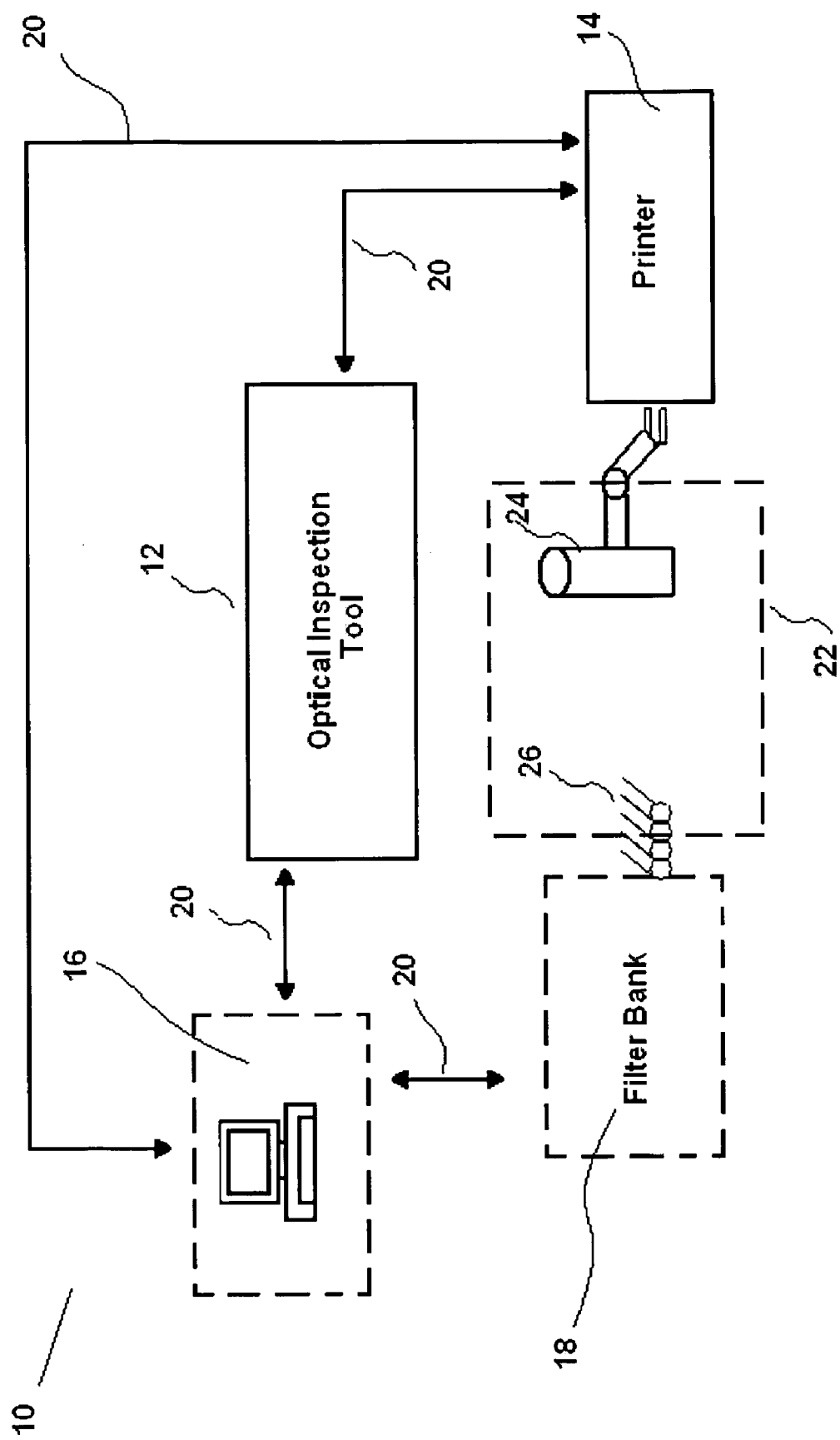
FIG. 1 illustrates an exemplary optical inspection system including a spatial mask printer and an optical inspection tool.

FIG. 1 illustrates an exemplary optical inspection system 10 including a spatial filter mask printer 14 operably connected to, or integrated as part of, an optical inspection tool 12. The optical inspection tool 12 may be used to obtain data to define a spatial filter image which is then printed by the printer 14 and used in the optical inspection tool 12. Alternative embodiments may include an imaging control computer 16 to supervise and/or control the inspection and printing processes and one or more internal and/or external filter banks 18 for storage of a plurality of previously-printed filters. One skilled in the art will recognize that data connections 20 are indicated for purposes of illustration only—the various components may be connected to a larger network and may be coordinated and controlled in a variety of ways. For instance, in one embodiment, a universal serial bus (USB) connection is used to link the printer to the imaging tool; particular data connections will vary dependent on the components that are ultimately used.

In one embodiment, the printer 14 is integrated with the optical inspection system 12 and/or filter bank 18 via an automated loading apparatus 22, which is configured to move a printed filter substrate from the printer into the optical inspection tool. In the exemplary loading apparatus 22 illustrated in FIG. 1, the filter substrate may be moved between the printer and the optical inspection system by robotic arms 24 and conveyor 26. One skilled in the art will recognize, of course, that other combinations and implementations of loading apparatus are possible using conventional robotics, and the present subject matter is not limited by such particular implementations. In systems in which robotics and conveyors would be uneconomical, for example, loading apparatus 22 could be reduced or eliminated, and an operator could remove a filter mask and load it into the optical inspection tool. However, use of automated apparatus at least in part is preferred to avoid possible contamination of the filter substrate and/or other equipment. In embodiments in which a printer and filter bank are incorporated into an inspection tool, loading apparatus 22 may also be located within the tool.

For example, as illustrated, robotic arm 24 can grab a printed filter substrate via grab points and pull the substrate out of the exit envelope of the printer. The arm can then rotate and extend to place the substrate into a loading slot of an optical inspection system, with the optical inspection system including a conveyor or other additional internal components to move the inserted filter into the optical path of an object being imaged. Conveyor 26 may be used to move a filter in or out of filter bank 18 for longer-term storage.

In an embodiment discussed further below, the printer 14 includes appropriate sealing and contaminant control components such that the printer can be used in close proximity to the optical inspection tool rather than outside the cleanroom environment. Such nearby use can save time and increase throughput, since printed filters would not have to be brought in and out of the clean room for use in the optical inspection tool. However, the printer may be located outside the cleanroom, inside the cleanroom, or even be integrated into the optical inspection tool itself without departing from the spirit of the discoveries set forth herein. Similarly, use of the filter bank may not be necessary depending upon a particular application, and in any event the filters may be stored near the inspection tool and printer or far away. In one embodiment discussed below, the inspection tool itself is adapted to receive and house a plurality of spatial filters.

Figure 2:
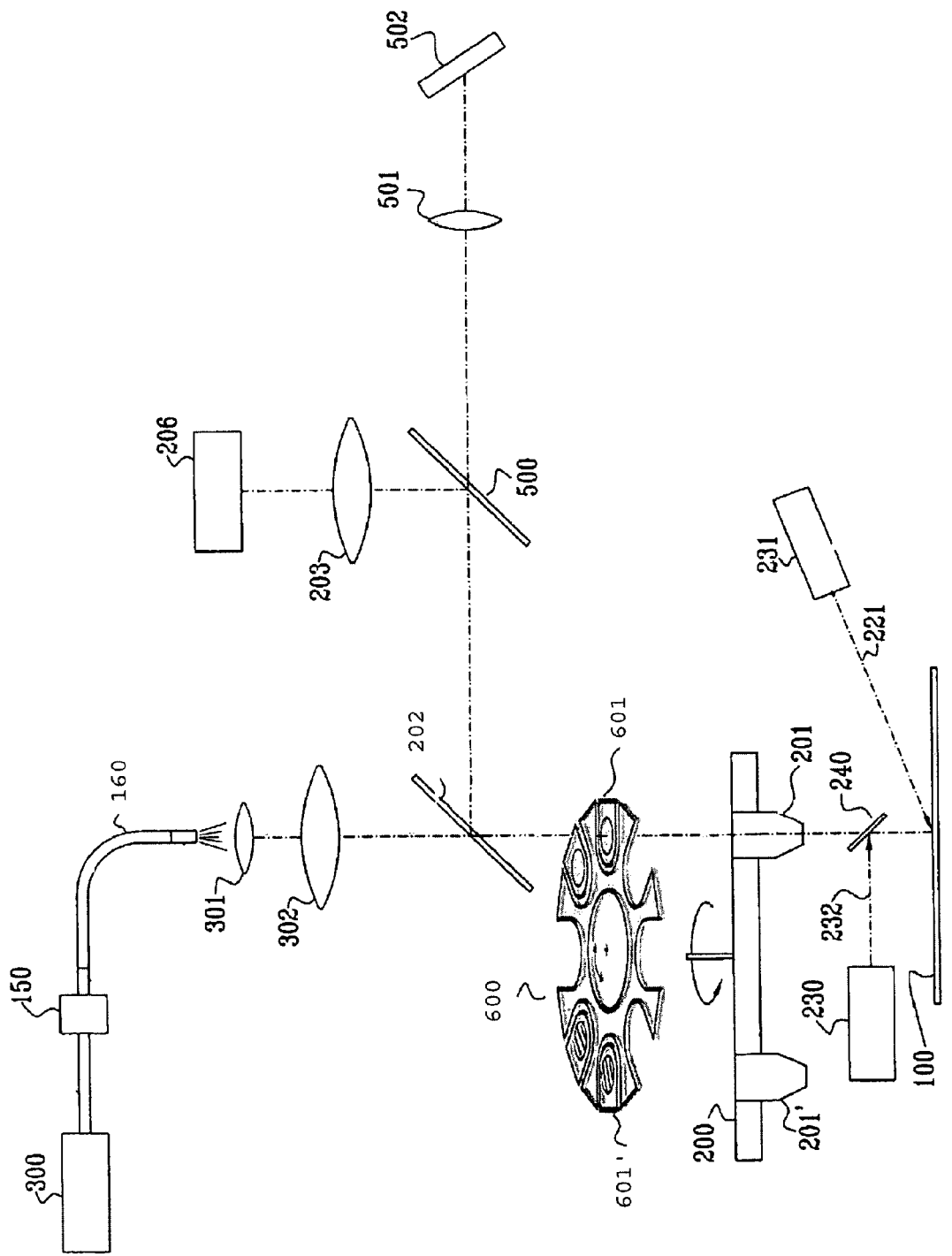
FIG. 2 illustrates an example of an optical inspection tool for use in accordance with the system disclosed herein.

FIG. 2 illustrates an exemplary optical inspection tool suitable for use in the presently-disclosed system, and similar to embodiments discussed in co-pending U.S. patent application Ser. No. 10/345,097 assigned to Negevtech, Ltd, and incorporated by reference herein in its entirety. As shown, the inspection tool includes an object under inspection 100, in this illustration, a wafer, illumination sources 230, 300 and 231, detectors 206 and 502, and a number of lenses. Although reference numerals 230, 231 and 300 are shown in conjunction with different components, 230, 231 and 300 can also represent varying the nature of light from a single source by different positioning or use of optical components.

The skilled artisan will, of course, recognize, that the present depiction of a wafer and particular inspection systems is for purposes of illustration only, as the invention disclosed herein is suitable for objects with repetitive aspects other than wafers, and is also suitable for use in other inspection systems and in conjunction with different optical tools, as well.

FIG. 2 is an overall schematic side view including the illumination system of a defect detection apparatus. According to different methods of operation, three alternative modes of illumination are provided: Bright Field (BF), Side-illuminated Dark Field (DF) and Orthogonal or Obscured Reflectance Dark Field (ODF). Each mode of illumination is used to detect different types of defects in different production process steps. For example in order to detect an embedded defect in a transparent layer, such as silicon oxide, BF illumination is preferred. In order to detect a small particle on a surface, DF illumination may yield better results.

In bright field illumination in general, the illumination is incident on the sample through the same objective lens as is used for viewing the sample. FIG. 2 shows a bright field illuminating laser source 300 delivering its output beam into an optical delivery fiber bundle 160, preferably by means of a laser to fiber coupler 150. This optical fiber bundle 160 serves the dual purposes of providing uniform illumination on the sample and for coherence breaking of the laser illumination. From the output termination of the fiber bundle 160, the laser beam is imaged by means of illumination transfer lenses 301, 302, onto the objective lens in use 201, which is operative to focus the illumination onto a wafer plane 100 being inspected. Appropriate alternative objective lenses 201' can be swung into place on an objective revolver 200, as is known in the microscope arts.

It will be noted that FIG. 2 further includes filter wheel 600 and illustrated mask filters 601 in the illumination path near objective lens 201; such mask filters will be discussed in due course. It will be presently recognized that mask filters 601 may be placed and removed from the illumination path as desired—for instance, a filter mask may not be needed in a typical bright field illumination test, and so filter wheel 600 could be rotated such that no filter lay in the illumination path.

The illumination returned from the wafer is collected by the same objective lens 201, and is deflected from the illumination path by means of a beam splitter 202, towards a second beam splitter 500, from where it is reflected through the imaging lens 203, which images the light from the wafer onto the detector 206. The second beam splitter 500 is used to separate the light going to the imaging functionality from the light used in other aspects of the inspection tool, such as the auto-focus detector 502 and related components.

When conventional dark field illumination is required for imaging, a dark field side illumination source 231 is used to project the required illumination beam 221 onto the wafer 100. When orthogonal dark field, or obscured reflectance dark field illumination is required for the imaging in hand, an alternative dark field illumination source 230 is used to project the required illumination beam 232 via the obscured reflectance mirror 240 onto the wafer 100 orthogonally from above.

As described herein, a repetitively pulsed laser source is preferably used in the illumination system, although CW laser illumination, other monochromatic, or semi-monochromatic illumination types may also be used. In accordance with the requirements of providing a high brightness light source that produces a directionally intense beam of short time duration and at high repetition rates the third harmonic of a Nd:YAG Laser output is preferably used. However, other types of repetitively pulsed illumination may be used, such as other harmonics, for example the fourth and fifth harmonics of the Nd:YAG Laser. Other lasers such as Excimer Lasers are also suitable.

The geometry of certain objects, such as semiconductor wafers, may consist of a large-scale multiply repetitive pattern that defines the dies of the wafer. Within each die, there are often areas in which there appears an array of a repetitive pattern with a cycle of a few µm, or a few cycles per micron. This occurs especially in memory chips or in the memory area in a logic chip. When coherent or partial coherent illumination is incident on such a periodic array, the array serves as a diffraction grating that reflects the light only in the defined Bragg angles. The reflected light produces a diffraction pattern of spots in the back focal plane of the objective lens.

The back focal plane is also referred to as the Fourier plane of the lens, since the image obtained in this plane is a two-dimensional Fourier transform of the object. One of ordinary skill in the art will recognize that Fourier planes may lie in several different spatial locations depending upon the optics of the particular system being utilized, and so the more general term "Fourier plane" is used below.

The smaller the cycle in the object plane, the larger the distance between the spots in the Fourier plane. The size of these spots depends on the optical quality of the objective lens, but even more on the nature of the incident light.

When the input light is a collimated beam, the spot size is very small. In U.S. Pat. No. 5,970,168 to Montesanto et al., for "Fourier Filtering Mechanism for Inspecting Wafers," incorporated in its entirety by reference here, there is described the use of a spring array as a Fourier plane filter, with a built-in damping mechanism to prevent interference from mechanical vibrations. However, Montesanto generally relates to use of a laser as the light source, which is a collimated coherent light source.

An extended source which need be only partially coherent, as used in the dark field side illumination embodiments of certain optical inspection tools, is used to produce defined spots in the Fourier plane. According to this method, when the illuminating beam is such an extended light source, the size and shape of each of the spots in the Fourier plane becomes a miniature image of the extended source. Furthermore, in order to produce the diffraction pattern in the Fourier plane, it is not necessary that each point in the extended source be a coherent source. This extended and partially coherent form of illumination is successful in generating a Fourier plane diffraction pattern array, because each separate area of the illuminating beam is made up of an assembly of self coherent spots, but unrelated to each other. This outcome may be achieved, for example, via optical treatment performed on the illuminating beam by means of imaging optics at the illumination source.

Furthermore, when the cycle of the repetitive pattern is sufficiently small, as in many semiconductor wafers, the spots do not overlap and cover only a relatively small part of the objective pupil. If the structural periodic information from the image can be filtered out, the optical information anomalies resulting from defects on the wafer can be revealed in the form of non-periodic information spread over a wide range of spatial frequencies. This is performed in practice by blocking the transmission of light specifically in the area of those spots, eliminating the information relevant to the repetitive pattern from the image from the remaining optical information transmitted past the Fourier plane, thus making it possible to detect anomalies caused by departures from the desired pattern on the wafer.

Figure 3A:
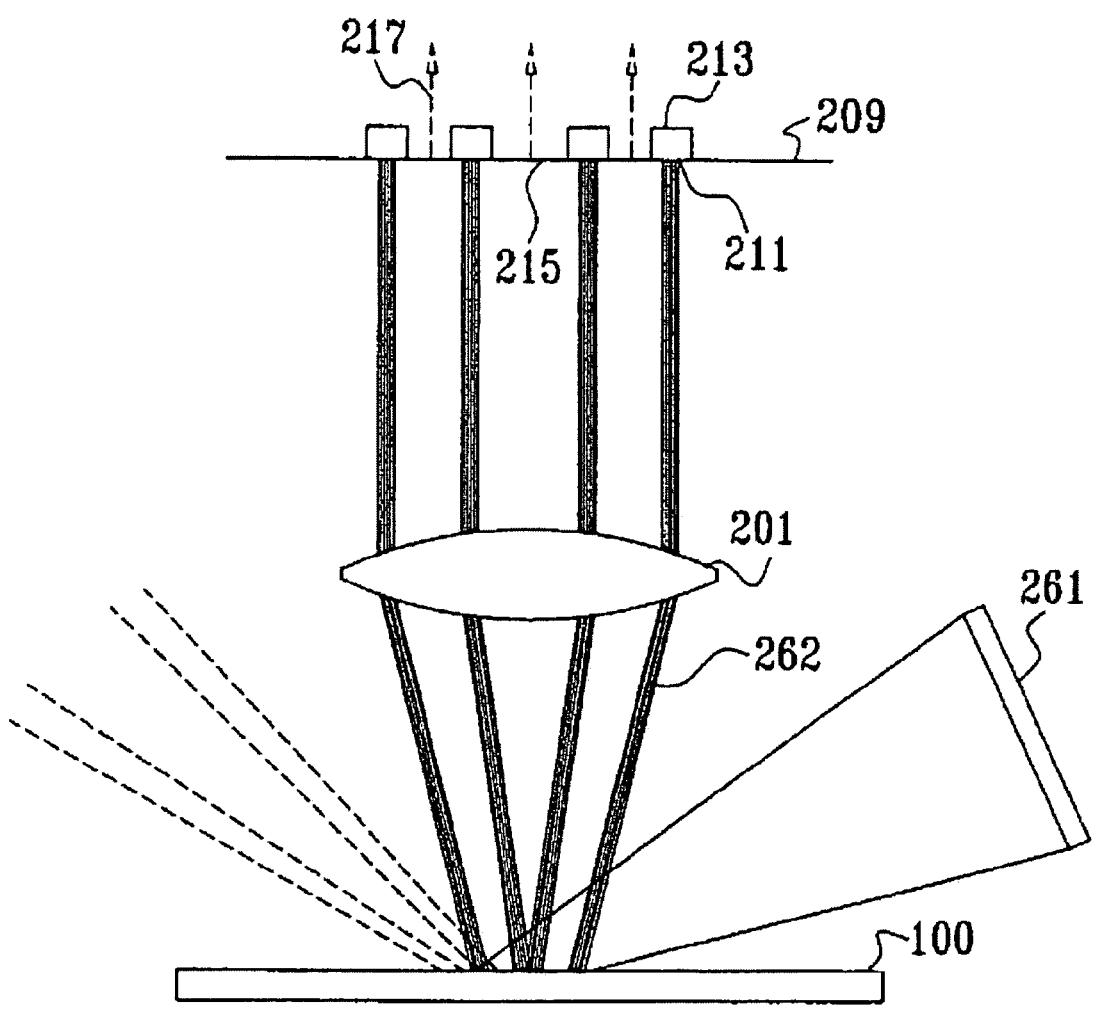
FIGS. 3A, 3B, and 3C illustrate the conceptual underpinning of the spatial filters made and used in accordance with the present invention.
Figure 3C:
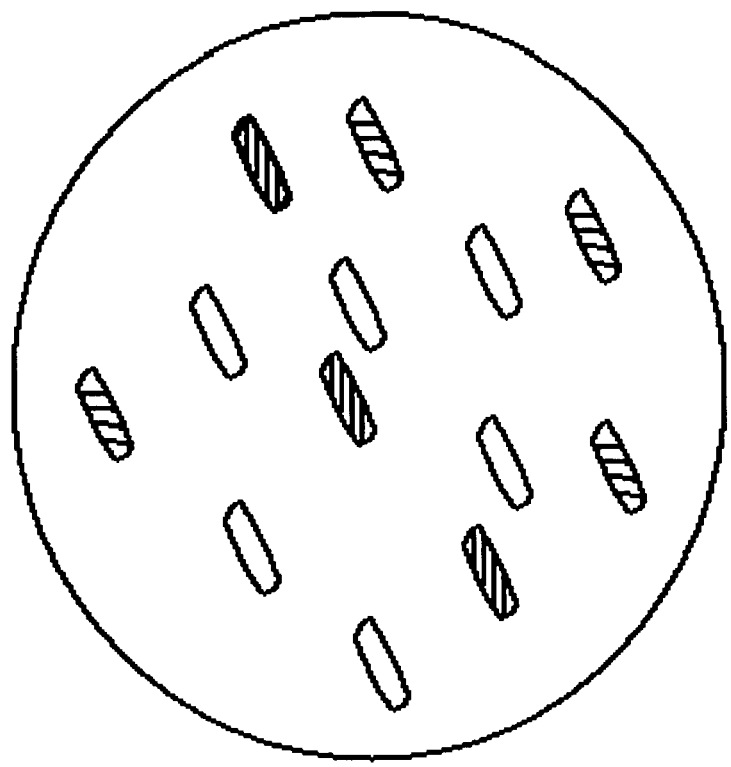
Figure 3B:
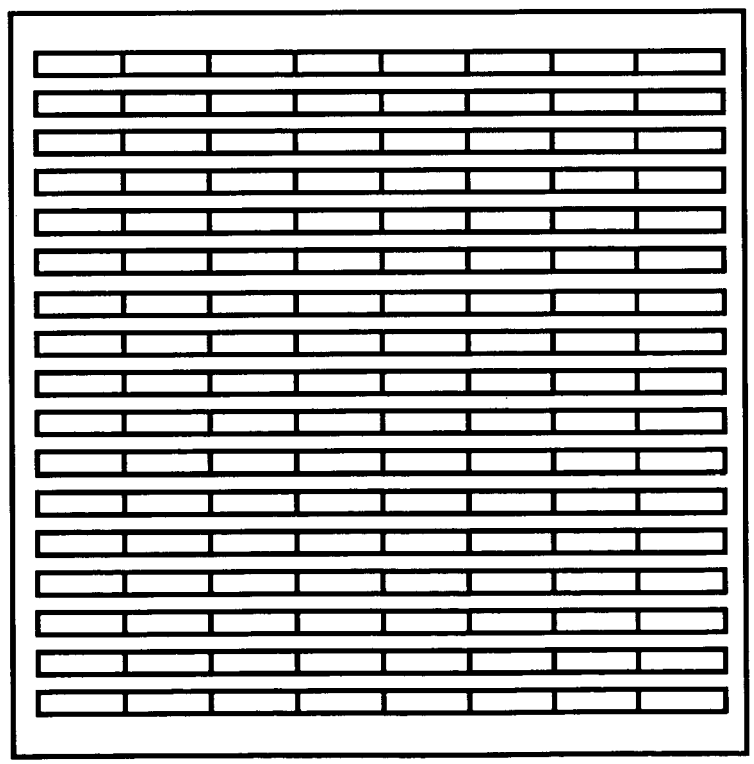

Reference is now made to FIG. 3A, which schematically illustrates a method for performing this procedure, and FIGS. 3B and 3C which depict an exemplary repetitive pattern and an exemplary Fourier plane image. The skilled artisan will note that the depictions of FIGS. 3B and 3C are for purposes of illustration only, and do not indicate an actual pattern and corresponding Fourier image.

Referring to FIG. 3A, an extended source 261, which can even be non-parallel, is incident on the wafer 100 under inspection, such as the wafer shown in FIG. 3B. The scattered light 262 from the wafer features is imaged by the objective lens 201. At the back focal plane 209 of this lens, which is the above-mentioned Fourier plane, there is generated a patterned array of spots 211 representing the repetitive features of the wafer being imaged by the scattered light. For instance, the array of spots may be similar to that shown in FIG. 3C, with the spots featuring differing degrees of brightness, as indicated in FIG. 3C by different cross-hatching.

Referring again to FIG. 3A, in the interstitial positions 215 between these spots, there may appear any light scattered from non-repetitive features on the wafer die, such as from a defect which it is desired to detect. A mask 213 may be constructed to block the light from the predetermined patterned array of spots 211 and disposed at the Fourier plane. The scattered light 217 from defects present on the wafer die will thus pass the Fourier plane to be imaged and detected by the system without interference from the expected repetitive features of the wafer die.

In order to adapt a spatial Fourier filter design to a specific layer, it is useful to view the image obtained in this plane. As noted above, while the Fourier plane is often the back focal plane of the objective, such back focal plane may inaccessible, as with many high power objective designs, and so an image of this plane can be used.

Figure 4:
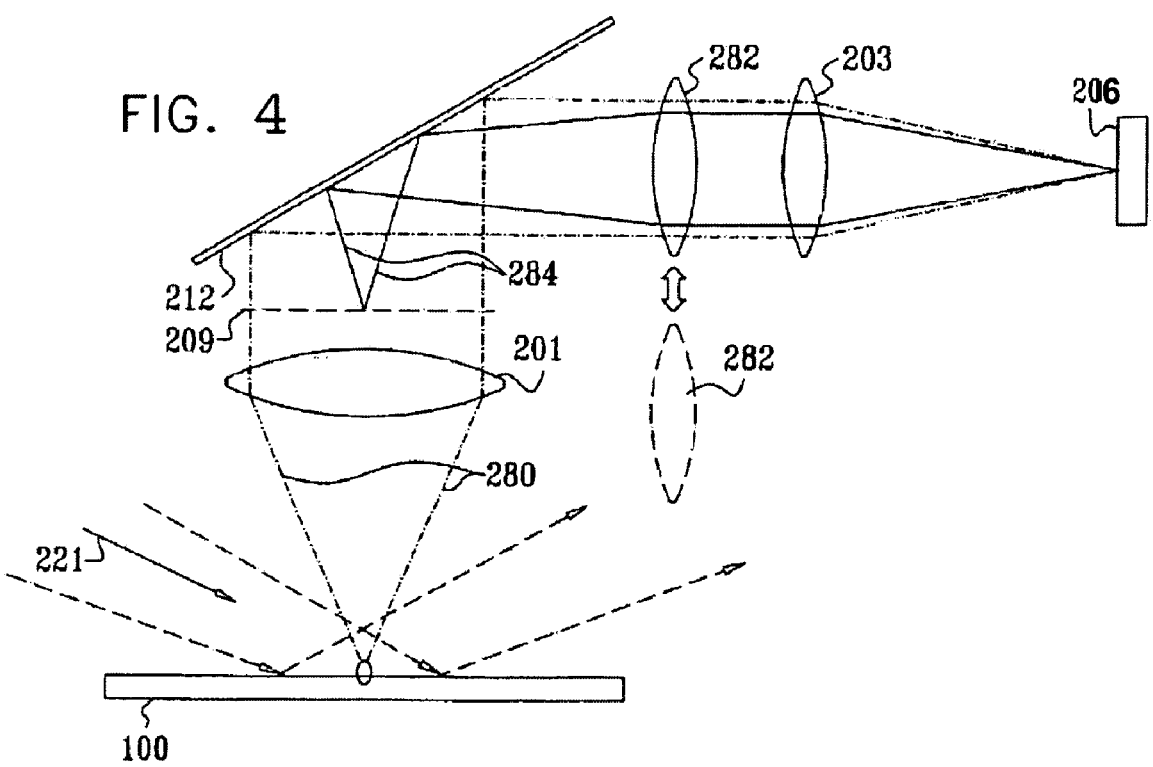
FIG. 4 illustrates an exemplary arrangement for obtaining Fourier images of an object for use in accordance with the present invention.

Reference is now made to FIG. 4, which illustrates an exemplary method by which this plane can be imaged onto an existing detector by introducing an additional lens into the imaging optics. In the embodiment of FIG. 4, dark field side illumination 221 is incident on the wafer 100, and the scattered light, as designated by the dashed lines 280, is collected by the objective 201, for imaging on the detector 206 by means of the detector imaging lens 203, all as previously described hereinabove.

In this illustration, the Fourier plane 209 is located behind the objective lens 201, and may be in a position where it is not easy to locate a detector for direct imaging. Therefore, when the Fourier plane has to be viewed in order to determine the correct Fourier plane filter to construct, an additional imaging lens 282, known as the Fourier imaging lens, is inserted into the imaging path such that the detector now images the Fourier plane 209. The solid lines 284 in FIG. 4 represent the optical imaging path from the Fourier plane to the detector, with the Fourier imaging lens in position. In this manner, the required pattern of the spatial filter in the Fourier plane for a specific die region can be designed according to the imaged field of the object.

As noted above, the resulting image will be a 2-dimensional Fourier transform of the object image and generally illustrate the frequency components of the imaged object. Of course, one of skill in the art will recognize that discussion herein of particular optical illumination and inspection tools and techniques is not intended to limit the Fourier filtering embodiments discussed herein, which may be adapted to multiple types of optical systems. The actual layout of the Fourier image will depend upon the optical characteristics of the imaged object and inspection tool used to generate the image. Certain object properties will immediately be apparent, however, such as the aforementioned spots due to periodicity of portions of imaged object's structure.

Figure 5:
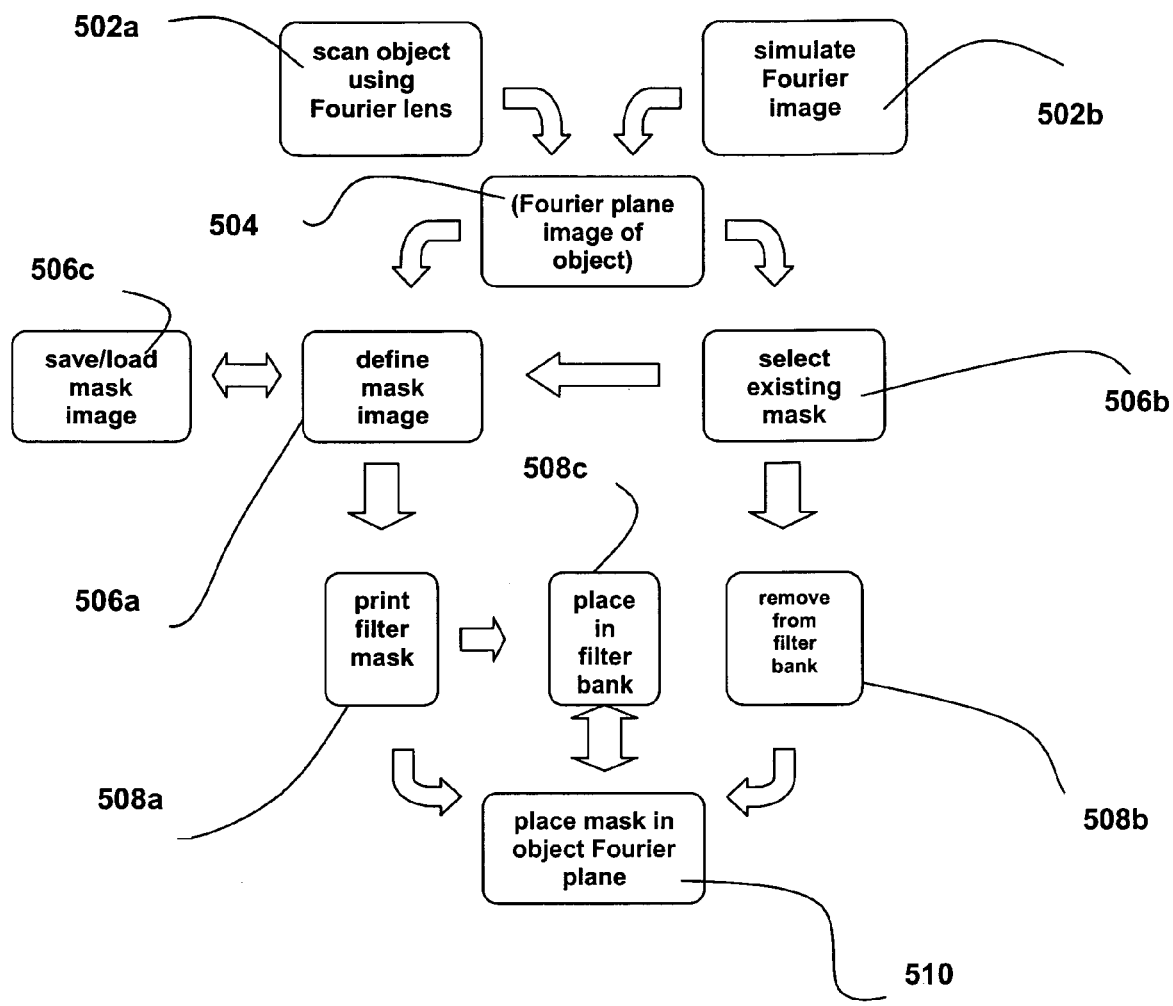
FIG. 5 is an exemplary flowchart illustrating embodiments of methods in accordance with the present invention.

The periodicity of the imaged structure can be used to produce a printed filter mask for use in an optical inspection system. FIG. 5 is a generalized, exemplary illustration of methods for Fourier filtering using a printed filter mask. As an initial matter, a representation of the object in the Fourier plane is obtained. For instance, the Fourier plane of an object may be imaged using an optical inspection system including a Fourier lens as discussed above as indicated at 502a in FIG. 5. Alternatively or additionally, the Fourier image or characteristics of the object may be simulated as shown at 502b based upon product data such as physical or structural information (such as memory cell size), SEM (scanning electron microscope) or other images, or other data representative of the object's physical characteristics.

As shown at 504, once a Fourier plane image, or other representation of the object, is obtained, a filter mask can be defined as shown at 506a or selected from a pre-existing group, as shown at 506b. A preexisting mask may be selected either by the user or automatically based on the Fourier characteristics of the object under inspection. The preexisting mask may then be selected from a bank, or a pre-existing mask image printed for use in the tool. For example, the system can be configured to automatically recognize a previously-inspected type of wafer and select an appropriate filter from a filter bank.

Returning to step 506a, in various embodiments, a user can observe the Fourier image and define a filter mask by specifying blocking areas based on the Fourier image. For example, the blocking areas may be drawn in a computer program where a drawing area overlays a Fourier image similar to that illustrated in FIG. 3C. As will be discussed in detail below, defining a filter mask can include simulating the effect of a filter on an object image using software, and may include designing a new filter from scratch or using standardized or previously-saved images or other elements.

506c illustrates that the filter mask image may be saved or loaded from memory or other media, such as a hard disk drive, during the design process. As noted above, the skilled artisan will recognize that although "images" are discussed, other representations of the object and filter mask Fourier characteristics may just as easily be implemented throughout the system; for instance, a mask may be stored as a digital image, or as another type of data file.

Furthermore, the degree of manual user interaction can vary without departing from the scope of the present invention. For instance, in some embodiments, a user manually draws in filter blocking elements to define a filter mask, while in others the filter mask may be defined partially or entirely by computer. Other embodiments feature a combination of manual and computer definition.

At step 508a, the defined filter mask image is sent to a filter mask printer. As will be discussed below, the printer may be networked with or incorporated into an optical inspection tool, and may be configured to operate in accordance with cleanroom requirements. Alternatively, as shown at 508b, an existing mask may be selected and removed from a filter bank housing a plurality of such masks.

In alternative embodiments, an existing mask may be modified. In such cases, an existing mask image is selected and altered to incorporate additional blocking elements. The existing filter mask corresponding to the existing mask image is then obtained and sent to the printer, which prints the additionally-defined elements on the filter mask. Alternatively, of course, an existing mask image that is modified can be printed as an entirely new mask.

In some embodiments, printing can also include producing or attaching an identification tag or label to the filter mask or associated equipment. The optical tool, filter bank(s), and handling apparatus may be configured to read such tag(s). Through use of such identification in conjunction with a database program, the filter masks, filter mask images, particular wafers, and particular wafer recipes may all be associated with one another to streamline the inspection process.

At 510, the mask is placed in the Fourier plane of the object being imaged. Depending upon the optical characteristics of a particular tool, the Fourier plane may lie in a number of different locations, and the mask should be placed accordingly. As an optional intermediate step 508c, printed masks may be placed into a filter bank when not in use. Filter banks may be included as part of an inspection tool or apart from the tool, and may be incorporated for use via automated loading apparatus such as robot arms and tracks, manual loading, or a combination of methodologies.

Further detail as to various exemplary embodiments of the present system and method discussed above will now be provided, returning first to the initial stage of defining a filter mask image.

To define a filter mask image, computer software on imaging computer 16, the inspection tool 12, or even another, possibly remote, computer interfaced to network 20 can be configured and used to generate a representation of the object's Fourier image and overlay a drawing area thereon. A user can then define blocking areas by drawing shapes, lines, and other markings—for instance, by tracing the brightest areas of the Fourier image and then filling them in. The computer software can provide for free hand drawing, pre-defined shapes, and other graphical manipulations. The user-defined areas may be completely opaque or have varying degrees of opacity depending upon the degree of filtering desired. The user-defined areas may then be stored as a computer file, such as a bitmap image, or in another suitable format.

Although discussions herein relate to the use of a filter with opaque areas to block selected portions of light from transmission through the filter, the skilled artisan will recognize that the present invention is equally applicable in other circumstances. For instance, during filter definition, the areas through which light will be transmitted may be defined, with areas to be blocked left blank. Reflective Fourier filters may be used such that the desired areas of light are reflected into appropriate inspection tool optics; in such a case, the blocking areas specify what parts of the filter should be rendered non-reflecting (or vice-versa). The software may include algorithms to convert filter designs applicable to one type of tool into a filter design suitable for another type of tool.

Alternatively to manual definition, the computer software may automatically generate, suggest, or define blocking area patterns or portions thereof based upon an analysis of the Fourier image characteristics. Analysis software can be configured to select a previously-existing filter mask image based upon such factors as an analysis of the Fourier image, an identification of the object being imaged, or the user-defined areas. The pre-existing stored filter mask image can be improved or altered by the user, or automatically by the computer.

In another alternative embodiment, the computer can generate simulations of the Fourier image before or after filtering. The simulations may be of the Fourier image of the object alone based upon an analysis of its physical characteristics input into the computer. For example, in an inspection of a wafer including memory cells, memory cell size or design parameters can be input into simulation software. A non-Fourier image (such as an optical or SEM-based image) could be used as the basis for a simulation of a corresponding Fourier image, as well. In such embodiments, an initial imaging of the Fourier plane may be omitted and the filter constructed based upon the simulated Fourier image from the object properties. Alternatively, the simulated Fourier image can be used in conjunction with an actual Fourier image during filter definition.

In a further alternative embodiment, simulations may be used to determine the results if a particular filter mask image design were to be used during imaging. When a user (or the computer) is designing a filter, the computer simulations and data can be used to generate feedback for the design process such as suggestions and warnings.

Once a filter mask image is defined, the image data can be used to generate a filter mask. In a preferred embodiment, the filter mask image is sent to a printer and the image is printed on a filter substrate. The substrate may comprise any suitable material, such as plastic, ceramic material, or glass. As noted above, depending upon the design of the particular inspection tool in which the filter will be used, the filter may be designed for a reflective material, with portions of an image for reflection into a detector and other portions blocked from reflection.

In one exemplary practice, the filter substrate comprises a 3.0 mm-thick, 48 mm-diameter circular window of fused silica polished to a high optical quality. Embodiments of the present invention can include those in which the silica is polished to a quality of $\lambda/60$, where $\lambda=633$ nm. The substrate may have a greater surface area than is ultimately usable, depending upon the system in which it is used. One of ordinary skill in the art will recognize that the filter surface area and shape preferably is taken into account in designing filter masks. Additionally, the physical and optical qualities of the filter masks and substrates can be varied by one of ordinary skill in the art in accordance with the particular optics and design of the imaging system in which the filter will be utilized.

Figure 6:
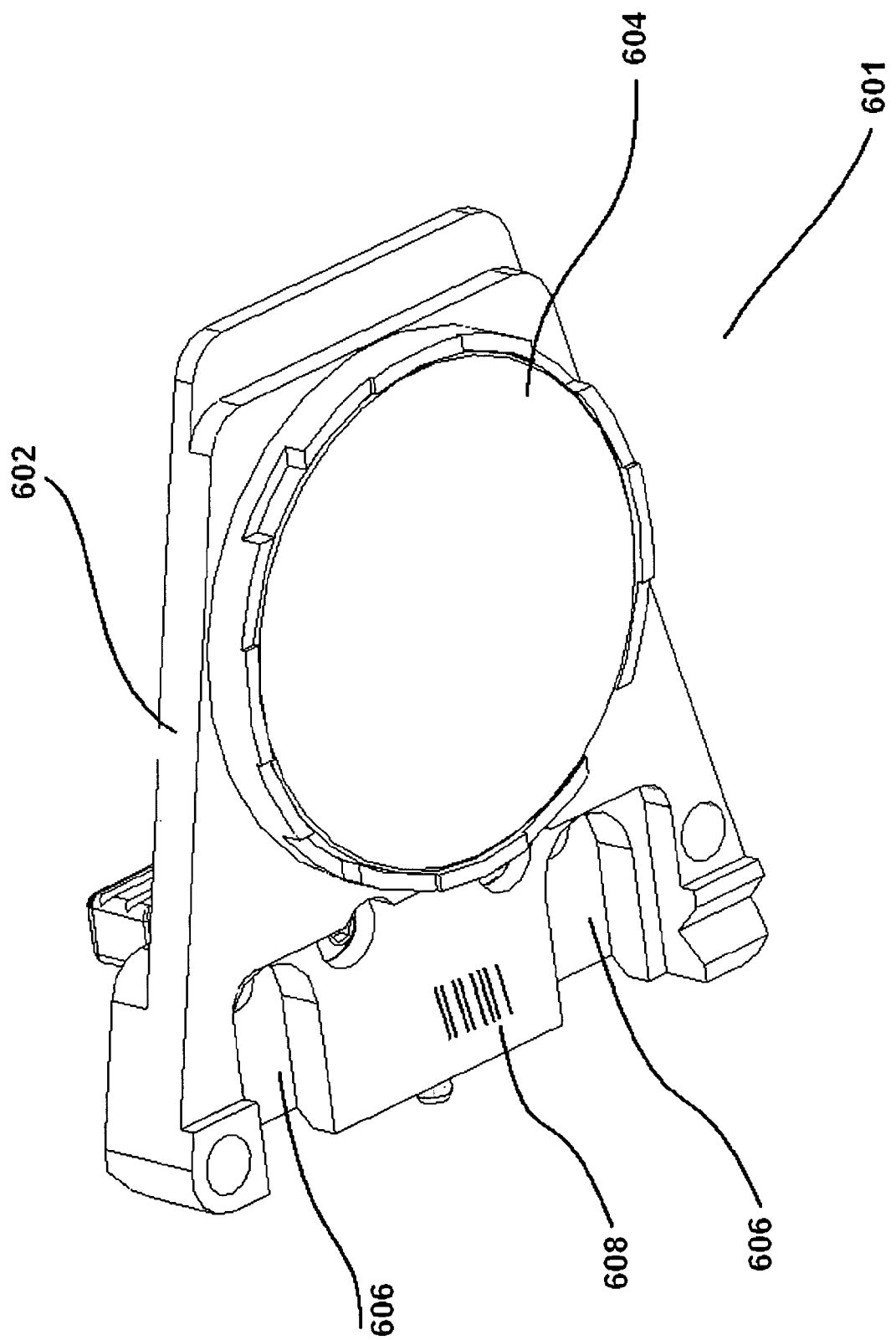
FIG. 6 illustrates an exemplary filter mask assembly for use in accordance with the present invention.

As illustrated in FIG. 6, the filter 601 may include a substrate 604 disposed in a frame 602, which may be constructed of any suitable rigid material(s), such as aluminum. The frame 602 shown in FIG. 6 includes grab points 606 such that the filter can be manipulated without contacting the substrate 604 and the attendant risks of smearing or otherwise introducing physical or optical contamination. The filter substrate may be bonded to the frame, or in an alternative embodiment may be removably attached to the frame via one or more latches, clips, or springs such that the filter substrate is secured to the frame for use but may be later separated.

The filter mask and/or its frame can further comprise one or more identification indicia 608, such as barcodes, alphanumeric characters, RFID tags, or other suitable identification markings. When identification indicia are used, the optical inspection tool, filter banks, and/or transport mechanisms may include appropriate circuitry to read the indicia and identify the filter.

Figure 7:
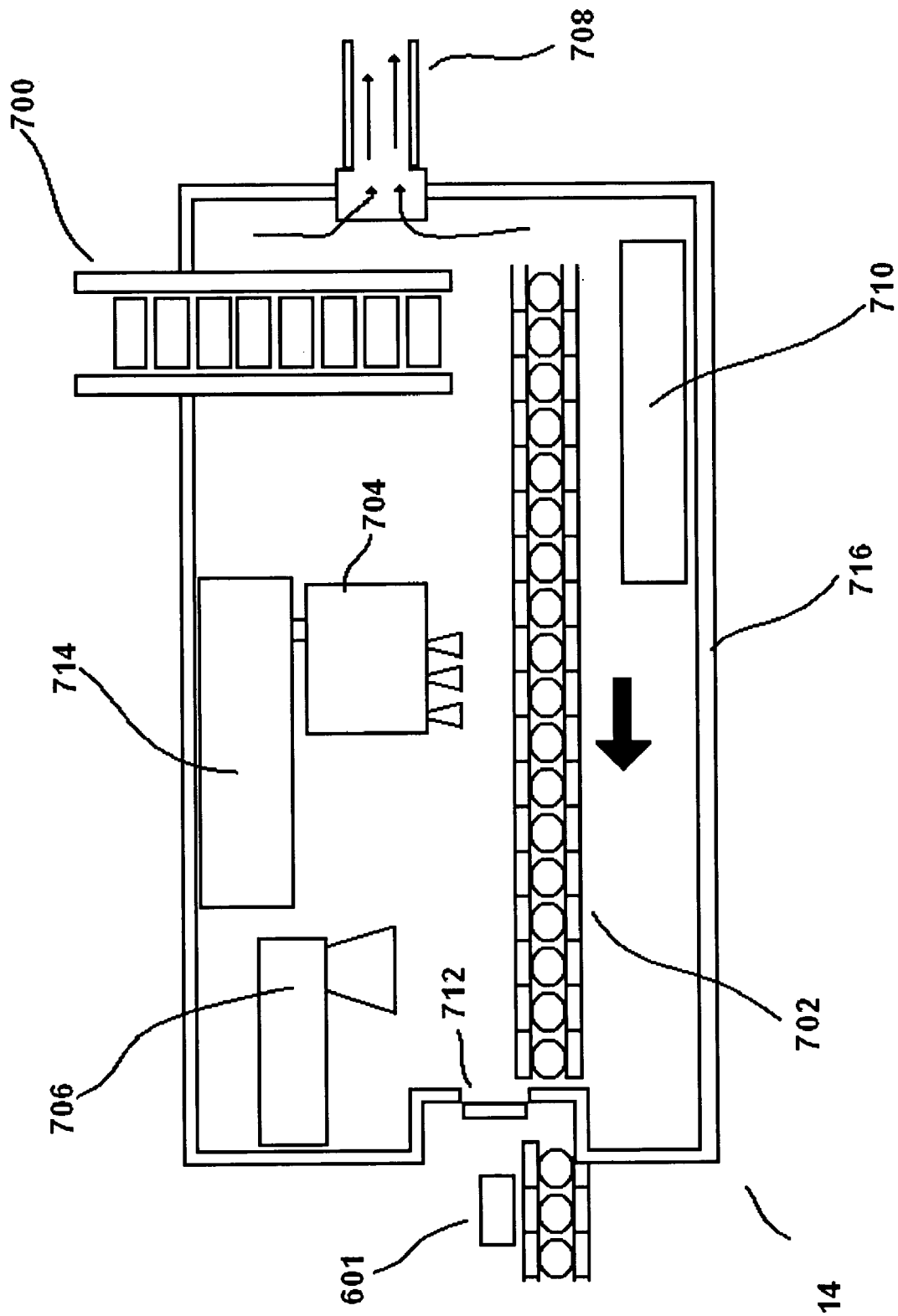
FIG. 7 illustrates an exemplary filter mask printer for use in accordance with the present invention.

In one embodiment, the mask printer 14 comprises an inkjet printer such as the one schematically illustrated in FIG. 7. The inkjet printer is used to apply any suitable ink to a filter substrate. In the exemplary embodiments discussed below, UV-curable ink and an inkjet printer are used, but other printing methods and/or other inks may be suitable (or adapted to be suitable) for use in producing printed spatial filters. One skilled in the art will recognize that the "printing" aspect should be understood to broadly refer to any automated rendering and fixation of the filter mask image on a suitable substrate.

As shown in FIG. 7, the printer includes a loading cartridge 700, a conveyor 702, at least one inkjet print head 704, UV curing lamps 706, and ventilation exhaust connections 708 and other apparatus interfaced to a fab air system.

The use of UV-curable ink in conjunction with inkjet printing in an appropriately configured printer allows possible contamination risks to be reduced, which may render the printer suitable for integration into an optical inspection tool or suitable for stationing nearby. Additionally, use of UV rather than heat curing reduces the risk of warping or distortion of the filter substrate and related deleterious effects on the optical qualities of the filter. For instance, UV-curable inks are cured by a polymerization that triggered by the UV light, rather than on solvent evaporation. Therefore, the amount of unwanted fumes and outgassing is reduced in such inks, which is an important consideration for fab-compatible processes. Additionally, UV-curable inks have been found to adhere more easily to glass substrates, which reduce wetting problems.

However, as noted above, such exemplary use of UV-curable ink and inkjet printing is not intended to be limiting. Other appropriately-adapted printing techniques, such as laser printing, etching, screen printing, and the like can be used on appropriate substrates in a manner that avoids distortion of the image and contaminants to the cleanroom environment. For instance, heat curing on a substrate sufficiently resistant to warping or in conjunction with a low-temperature-cured ink may be suitable. The printer also could be configured for use with inks cured by other means, such as microwave or infrared techniques. Preferable characteristics in alternative inks include cleanliness, long shelf life, little or no outgassing or other contaminants, and the ability to wet the chosen substrate without balling up.

As shown in FIG. 7, the UV-curable ink is stored in a cartridge 714, which may be removable, and can be applied by one or more inkjet heads 704 and then subsequently cured by one or more UV lamps 706. The spatial filter printer may also include a waste/purge tank 710 and appropriate connections to collect and store waste and byproducts of the printing process.

The printing resolution is preferably 150 dpi, although other resolutions may be utilized. One of skill in the art will recognize that one of the advantages of printed Fourier filtering is that the potential resolution of filters may increase as printing technology advances, and so higher resolutions are entirely within the purview of the present invention (along with lower resolutions, of course). The ink preferably is selected so that the printed areas will be sufficiently opaque to block desired wavelengths of light, such as those used by optical inspection tool in which the filter will ultimately be utilized. In one embodiment, black ink is used so that opaque areas have an optical density higher than OD3—that is, the opaque areas preferably allow less than $\frac{1}{1000}$ of the light to be transmitted—for 355 nm light. Other colors may, of course, be suitable for a particular system or application.

During the printing process, the conveyor 702 may move the filter substrate blank from the loading area 700 to the inkjet head or heads, and then on to the UV lamps for curing. The conveyor can then provide the printed substrate to an exit port 712.

In one embodiment, the exit port is a substantially sealed exit envelope, and all other printer components are housed in a substantially sealed case 716 to prevent escape of contaminants, such as stray ink and other particles. The printer case further includes ventilation connections 708 configured to interface with conventional clean room exhaust systems so that the printer case may be maintained at a slight underpressure relative to the outside. In this manner, the printer is further suitable for positioning in the clean room proximate an optical inspection tool, or may be integrated as part of the tool itself—the fumes and particles of the printing process are evacuated from the printer, and the completed substrate exits the printer through the exit port ready for use in an inspection tool.

Once a spatial filter mask is designed and produced, it can be placed in the Fourier plane of the object under inspection. In the optical inspection tool of FIG. 2, this placement is illustrated by filter wheel 600. Filter wheel 600 includes a plurality of receptacles for receiving spatial filter masks 601, and as noted above, may include a "blank" area for use when no mask is needed. A particular mask 601 can be selected for use and the wheel rotated to place the mask in the Fourier plane of the object under inspection. In this manner, the non-transparent areas of the filter mask will block portions of the object image and the relative intensity of the unfiltered portions, such as those attributable to defects, may stand out more readily at the detector.

Figure 8:
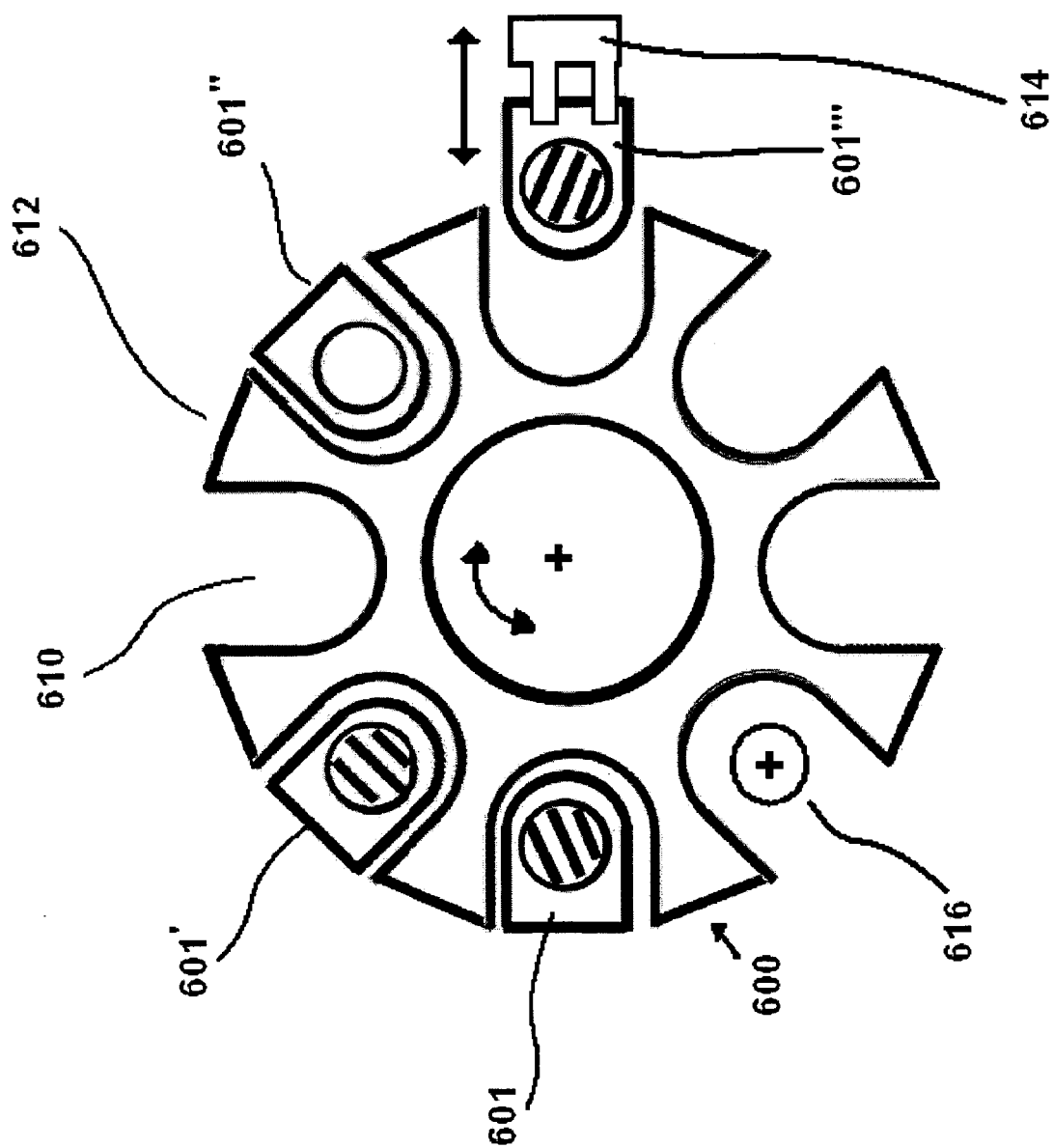
FIG. 8 illustrates one exemplary type of filter bank, namely, a filter wheel used in accordance with the present invention.

FIG. 8 illustrates one exemplary embodiment (600) of a filter wheel similar to that generally shown in FIG. 2, but in greater detail and as viewed coaxially with the optical path, rather than from the side as in FIG. 2. Filter wheel 600 as illustrated includes eight filter stations 610, although the number of filter stations may be varied. For example, in another embodiment, a 14-station filter turret is used. Stations 610 may be defined by side members 612, and include a slot, shelf, or other suitable support structure such that various filter assemblies 601, 601', 601'', 601''' may be securely supported while in the filter wheel. The particular mechanism for securing and supporting the filters is unimportant so long as the filters are adequately held in place and not misaligned when filter wheel 600 is rotated or when other filters are added or removed from the wheel. In certain embodiments, the filter assembly frames are sized and machined such that the filters fit snugly into stations 610 between side members 612.

Filter wheel 600 is positioned within an optical inspection tool such that it may be rotated about its axis by appropriate mechanisms, such as a servo motor. The amount of rotation can be selected so that desired stations 610 are moved to align selected filters 601, 601', and 601'' in the optical path of the inspection tool, shown here as a ray 616. In one embodiment, a station 610 is preferably kept empty for use in testing operations in which no filter is desired, such as bright-field illumination tests performed using tools such as the one illustrated and discussed in conjunction with FIG. 2.

FIG. 8 further illustrates loading apparatus 614, shown here as an end-gripper of a robotic arm. An optical inspection tool that includes filter wheel 600 may further include appropriate loading mechanisms to provide for automated insertion or removal of filters from the filter bank. Although 614 is shown here as a part of a robotic arm, the filter may be loaded into the wheel via a track, conveyor, or other suitable means known to one of skill in the art. Alternatively, an operator can manually load the filter into the filter wheel. The loading mechanism 614 or the filter wheel 600 may further include barcode, RFID, optical, or other scanners or input devices to read identification indicia associated with each filter in order to identify the filter loaded in stations 610.

The skilled artisan will recognize that a filter wheel is but one possible way to place the filter in the Fourier plane. For example, in an alternative embodiment an optical inspection tool could be configured to receive a single spatial filter at a receptacle and move the filter into place via conveyors, tracks, or other apparatus. Other embodiments could utilize both a filter wheel and a conveyor system to relay filters in and out of receptacles on the filter wheel, or could utilize multiple selectable filter wheels.

The filter wheel is illustrative of but one type of filter bank which may be used in accordance with the present invention. Collections of filters may, of course, be housed in a variety of containers in a variety of configurations, which are generally referred to as filter banks. For instance, another type of filter bank could comprise a stack or cassette of filters. Filter banks may be indexed or otherwise provide for identification of a particular filter or filters stored within the bank; for instance, a filter bank can be configured to identify filters stored therein based upon identification indicia associated with the filter mask and/or frame as discussed above. Filter banks may include components for automated loading, unloading, or other handling of filter substrates. A filter bank may be directly interfaced with an inspection tool or tools, printer(s), or other handling apparatus. Additionally, wheels and other filter banks may be configured to hold other filters beyond those made using a local printer, including even non-printed filters, or other optical components.

As noted previously, the particular optics of an inspection tool may result in variously-located Fourier planes beyond the back focal plane of an objective lens. Accordingly, a printed filter mask can be positioned as appropriate within an optical inspection tool to achieve the desired blocking effect. Moreover, although a particular inspection tool was presented for exemplary purposes, the methods and systems disclosed herein may be used with a variety of different optical inspection tools. For instance, although a transparent filter with opaque blocking elements was depicted, the skilled artisan will appreciate the teachings herein are equally applicable to other filtering methodologies, such as a reflectance-based filter wherein desired portions of an image are reflected towards a detector and non-desired portions blocked. As another example, although not discussed in conjunction with the exemplary tool shown in FIG. 2, the optics of a particular tool may be configured to provide for bright-field testing in conjunction with a Fourier filter.

The skilled artisan will further note that a particular object to be imaged may require more or fewer filters depending upon factors including the size of the object and the field of view of the optical inspection tool. Various combinations of filters may ultimately be used in an inspection—to provide one example, a group of semiconductor wafers may include wafers of two differing repetitive patterns. Appropriate filter masks may be designed and printed, and then hot-swapped during the inspection process while the optical inspection tool switches between different types of wafer. In the exemplary inspection tool of FIG. 2, such hot-swapping would be accomplished by rotating the filter wheel 600.

The filter masks housed in the filter wheel or other filter banks may be printed in advance based upon initial sample wafers and stored in filter bank(s) or may be prepared when the wafers are provided to the inspection tool, depending upon the ultimate testing and production circumstances. Additionally, the filter wheel or other banks may be configured to house non-printed filter masks, and other masks and optical components.

Although the filter masks and optical inspection tool and system discussed herein have been directed to inspection of defects in semiconductor wafers, it will be apparent that the tools and techniques are applicable to optical inspection of any other material which includes repetitive features. The teachings are also applicable to use of such filters in tools other than the exemplary inspection tool discussed above.

It is appreciated by persons skilled in the art that the present invention is not limited by what has been particularly shown and described above. Rather, as set forth in the attached claims, the scope of the present invention includes both combinations and sub-combinations of various features discussed herein, along with such variations and modifications as would occur to a person of skill in the art.

The invention claimed is:

1. A method of producing a spatial filter mask, comprising:
    producing an actual Fourier image representation of an object;
    producing a simulated Fourier image representation of the object based on an analysis of the actual Fourier image of the object;
    defining a filter mask image that includes at least one blocking area using the simulated Fourier image, wherein the blocking area corresponds to a representation of at least one repetitive aspect of the object; and
    printing a pattern corresponding to the filter mask image on a filter substrate;
    wherein the printing is performed in a substantially sealed case housing that includes ventilation connections, and wherein the ventilation connections are interfaced with an exhaust system so that a pressure inside the sealed case housing is lower than a pressure outside the sealed case housing.

2. The method of claim 1, wherein the printing comprises inkjet printing.

3. The method of claim 2, wherein the pattern is printed in UV-curable ink.

4. The method of claim 1, wherein the filter mask image comprises a digital image.

5. The method of claim 1, wherein the specifying includes drawing the at least one blocking area in a bitmap, and the printing includes inkjet-printing the drawn area.

6. An optical inspection system, comprising:
    an imager operative to obtain an actual Fourier image an object;
    a computer operative to produce a simulated Fourier image representation of the object based on an analysis of the actual Fourier image of the object and define a filter mask image that includes at least one blocking area using the simulated Fourier image, wherein the blocking area corresponds to a representation of at least one repetitive aspect of the object;
    an object illumination source;
    a filter mask printer enclosed in a substantially sealed case housing that includes ventilation connections, and wherein the ventilation connections are interfaced with an exhaust system so that a pressure inside the sealed case housing is lower than a pressure outside the sealed case housing the filter mask printer being configured to print the filter mask on a filter substrate; and
    positioning apparatus configured to move the filter mask into the imager, such that the filter mask is disposed at a Fourier plane of the optical inspection system.

7. The system of claim 6, wherein the filter mask printer comprises:
    a loading stage configured to hold at least one filter mask substrate; and
    a printing stage comprising at least one inkjet printing head.

8. The system of claim 6, further comprising a filter bank configured to receive a plurality of filter masks.

9. The system of claim 8, wherein the filter bank comprises a motorized wheel configured to receive a plurality of filters such that at least one filter can be selected and disposed at the Fourier plane by rotating the wheel.

10. The system of claim 8, wherein the positioning apparatus includes at least one robotic arm or conveyor configured to receive and transport a mask output from the filter mask printer.

11. The system of claim 6, wherein the filter mask is part of a spatial filter mask assembly, comprising:
    a filter substrate; and
    blocking areas comprising ink printed on the filter substrate in a pattern corresponding to a Fourier image produced by at least one repetitive aspect of a semiconductor device.

12. The system of claim 11, wherein the spatial filter mask assembly further comprises a frame.

13. The system of claim 12, wherein the frame further includes at least one spring clip such that the filter substrate is removably attached to a filter substrate holder.

14. The system of claim 11, wherein the ink comprises UV-cured polymer ink.

15. The system of claim 11, wherein the spatial filter mask assembly further comprises identification indicia.

16. The system of claim 15, wherein the identification indicia is selected from a group consisting of a barcode, alphanumeric characters, and a radio frequency identification (RFID) tag.

17. A method of Fourier filtering, comprising:

using an optical inspection system to create an actual Fourier image of an object;

using a computer to create a simulated Fourier image representation of the object based on an analysis of the actual Fourier image of the object;

defining a filter mask image that includes at least one blocking area using the simulated Fourier image, wherein the blocking area corresponds to a representation of at least one repetitive aspect of the object;

creating a spatial filter mask by printing the filter mask image on a filter substrate, wherein the printing is performed in a substantially sealed case housing that includes ventilation connections, and wherein the ventilation connections are interfaced with an exhaust system so that a pressure inside the sealed case housing is lower than a pressure outside the sealed case housing; and placing the spatial filter mask in a Fourier plane of the optical inspection system such that the spatial filter mask blocks a portion of the Fourier image of the object.

18. The method of claim 17, wherein the placing is performed by automated machinery.

19. The method of claim 17, wherein the printing comprises applying UV-curable ink to the filter substrate using at least one inkjet print head.

20. The method of claim 17, wherein the placing includes selecting the spatial filter mask from a plurality of spatial filter masks and automatically moving the selected spatial filter mask into the Fourier plane.

21. The method of claim 20, wherein selecting and automatically moving the spatial filter mask includes rotating a motorized wheel configured to hold the plurality of spatial filter masks such that the selected spatial filter mask is placed in the Fourier plane.

* * * * *

UNITED STATES PATENT AND TRADEMARK OFFICE
CERTIFICATE OF CORRECTION

PATENT NO.        : 8,031,931 B2
APPLICATION NO.   : 11/410276
DATED             : October 4, 2011
INVENTOR(S)       : Dan T. Fuchs and Shai Silberstein It is certified that error appears in the above-identified patent and that said Letters Patent is hereby corrected as shown below:

Title Pg, Item (75) Inventors:

"Silberstein, Shai (Risbon Le-Zion, IL)", should read -- Silberstein, Shai (Rishon Le-Zion, IL) --

Signed and Sealed this
Sixth Day of December, 2011

David J. Kappos
*Director of the United States Patent and Trademark Office*